US007754153B2

(12) United States Patent
Miyamoto et al.

(10) Patent No.: US 7,754,153 B2
(45) Date of Patent: Jul. 13, 2010

(54) OPTICAL BIOSENSOR FOR BIOMOLECULAR INTERACTION ANALYSIS

(75) Inventors: Tetsuro Miyamoto, Kasumigaura (JP); Mami Hakari, Mito (JP); Shigenori Togashi, Abiko (JP)

(73) Assignee: Hitachi, Ltd., Tokyo (JP)

( * ) Notice: Subject to any disclaimer, the term of this patent is extended or adjusted under 35 U.S.C. 154(b) by 861 days.

(21) Appl. No.: 11/441,076

(22) Filed: May 26, 2006

(65) Prior Publication Data

US 2006/0269966 A1    Nov. 30, 2006

(30) Foreign Application Priority Data

May 30, 2005    (JP)    ............. 2005-156548

(51) Int. Cl.
 G01N 21/00    (2006.01)
 G01N 21/62    (2006.01)
 G01N 21/63    (2006.01)
(52) U.S. Cl. ............. 422/82.09; 422/82.05; 436/164; 436/165; 436/171
(58) Field of Classification Search ............. None
 See application file for complete search history.

(56) References Cited

U.S. PATENT DOCUMENTS

| 6,268,125 | B1 * | 7/2001 | Perkins ............. 435/5 |
| 6,331,276 | B1 * | 12/2001 | Takei et al. ............. 422/82.09 |
| 7,394,547 | B2 * | 7/2008 | Tan et al. ............. 356/480 |
| 2003/0205664 | A1 * | 11/2003 | Abe et al. ............. 250/214 R |

FOREIGN PATENT DOCUMENTS

JP    03237966 A    * 10/1991
WO    WO 01/69209    9/2001

OTHER PUBLICATIONS

Johansen et al., "Imaging surface plasmon resonance sensor based on multiple wavelengths: Sensitivity considerations", Review of Scientific Instruments, AIP, Melville, NY, US, vol. 71, No. 9, Sep. 1, 2000, p. 3530-3538.

(Continued)

*Primary Examiner*—Unsu Jung
(74) *Attorney, Agent, or Firm*—Brundidge & Stanger, P.C.

(57) ABSTRACT

Biomolecular and other interactions are analyzed with a simpler construction. A biotic sample is fixed to noble metal nanoparticles, and light is irradiated from a light source to the noble metal nanoparticles through an optical fiber. Light obtained after reflection of the irradiated light by the noble metal nanoparticles is introduced to one or more optical detecting units through another optical fiber. The optical detecting unit(s) separately measure the intensity of the input light in a second band including a maximum absorption wavelength, a first band covering a longer wavelength range than the range covered by the second band, and a third band covering a shorter wavelength range than the range covered by the second band.

5 Claims, 4 Drawing Sheets

OTHER PUBLICATIONS

Ho et al., "Application of white light-emitting diode to surface plasmon resonance sensors", Sensors and Actuators B, Elsevier Sequoia S.A., Lausanne, Ch, vol. 80, No. 2, Nov. 20, 2001, p. 89-94.

Suzuki et al., "Development of novel optical waveguide surface plasmon resonance (SPR) sensor with dual light emitting diodes", Sensors and Actuators B, Elsevier Sequoia S.A., Lausanne, Ch, vol. 106, No. 1, Apr. 29, 2005, p. 383-387.

Haglmüller J. et al,. "Nanocluster Optical Resonance Devices for Molecular Structure Transduction", Current Nanoscience, vol. 1, No. 1, Jan. 2005, pp. 3-16.

Jenison et al., "Interference-based detection of nucleic acid targets on optically coated silicon," Nature Biotechnology, Nature Publishing Group, New York, NY, US, vol. 19, No. 1, Jan. 1, 2001, pp. 62-65.

* cited by examiner

OPTICAL BIOSENSOR FOR BIOMOLECULAR INTERACTION ANALYSIS

BACKGROUND OF THE INVENTION

1. Field of the Invention

The present invention relates to an optical biosensor for biomolecular interaction analysis. More particularly, the present invention relates to a measuring device and method for biomolecular interaction analysis, which are suitable for use in medical diagnoses, food inspection, etc.

2. Description of the Related Art

The principle for analyzing biomolecular interactions is described in Non-Patent Document 1 (Kazuhiro Nagata and Hiroshi Handa, "Real Time Analysis Experimentation for Interactions between Biological Substances", pp. 13-26, Springer Verlag Tokyo). In this document, to fabricate an immunity sensor or a gas sensor utilizing surface plasmon resonance (SPR), a compression wave of free electrons is excited to cause resonance at an interface between a metal thin film and a dielectric while propagating along the interface.

Another example for analyzing biomolecular interactions is disclosed in Patent Document 1 (JP,A 2002-365210). A biomolecule detecting method disclosed in Patent Document 1 is intended to simply analyze biomolecular bonds in a liquid by irradiating light at a particular angle to a substrate on which noble metal nanoparticles are held in solid phase, and measuring an absorption maximum wavelength of the specular reflection light.

SUMMARY OF THE INVENTION

In the SPR-based analysis method described in Non-Patent Document 1, a resonance incident angle is measured by using a prism on which the metal thin film is formed. To measure the resonance incident angle with high accuracy, however, the positional relationship among a light source of the irradiation light, the metal thin film, and a light detector has to be held with high accuracy during operation of a measuring device. Also, the SPR process is sensitive to temperature and entails the necessity of controlling respective temperatures of a sample to be measured and the whole of the measuring device with high accuracy, or of making correction depending on temperature. On the other hand, the biomolecule detecting method disclosed in Patent Document 1 has succeeded in realizing considerable simplification, but an improvement is still demanded in point of cost because it requires a relatively expensive device, such as a spectrophotometer.

In view of the above-mentioned problems with the related art, one object of the present invention is to enable biomolecular interactions to be analyzed by a small and simple device. Another object of the present invention is to enable biomolecular interactions to be analyzed at a lower cost.

To achieve the above objects, a measuring device for biomolecular interaction analysis according to the present invention is featured in comprising an optical biosensor having a surface of which optical characteristics are changed with adsorption of a substance onto the surface; and an optical measuring device for measuring the optical characteristics of the surface of the optical biosensor.

In the above measuring device for biomolecular interaction analysis, the optical measuring device is preferably capable of measuring the intensity of light in a preset wavelength band. More preferably, the optical measuring device is capable of measuring the intensity of light outputted from the optical biosensor in a second band including a maximum absorption wavelength, a first band covering a longer wavelength range than the maximum absorption wavelength, and a third band covering a shorter wavelength range than the maximum absorption wavelength.

The measuring device for biomolecular interaction analysis may further comprise a light source for irradiating light to the optical biosensor, and a filter allowing passage of light only in a particular wavelength band and disposed in the optical measuring device. The light source may have a light emission characteristic in a particular wavelength band. Further, the measuring device for biomolecular interaction analysis may include a plurality of light sources having characteristics to emit lights in respective different wavelength bands, and a controller for synchronizing a light emission time of each of the plurality of light sources with a measurement time of the optical measuring device.

Also, to achieve the above objects, a measuring method for biomolecular interaction analysis according to the present invention is featured in comprising the steps of fixing a biotic sample to noble metal nanoparticles, irradiating light from a light source to the noble metal nanoparticles, and introducing light obtained after reflection of the irradiated light by the noble metal nanoparticles to a plurality of optical detecting units, wherein the optical detecting units separately measure the intensity of the light inputted to the optical detecting unit in a second band including a maximum absorption wavelength, a first band covering a longer wavelength range than the maximum absorption wavelength, and a third band covering a shorter wavelength range than the maximum absorption wavelength.

In the above measuring method for biomolecular interaction analysis, preferably, the light irradiated from the light source is white light, the first band is a red band, the second band is a green band, and the third band is a blue band. Further, the irradiation light from the light source may be introduced to the noble metal nanoparticles immersed in a running buffer through an optical fiber, and the reflected light from the noble metal nanoparticles may be introduced to the optical detecting units including photodiodes and filters through an optical fiber different from the optical fiber through which the irradiation light is introduced.

According to the present invention, since a change of the intensity of the reflected light due to a shift of the absorption wavelength is measured by using the noble metal nanoparticles and the amount of the change is measured with attention focused on a particular wavelength within the measurement wavelength range, the measurement comparable to the case of using a spectrophotometer can be performed with a simpler device construction. Further, the measuring device can be reduced in size and cost.

DESCRIPTION OF THE PREFERRED EMBODIMENTS

Figure 1:
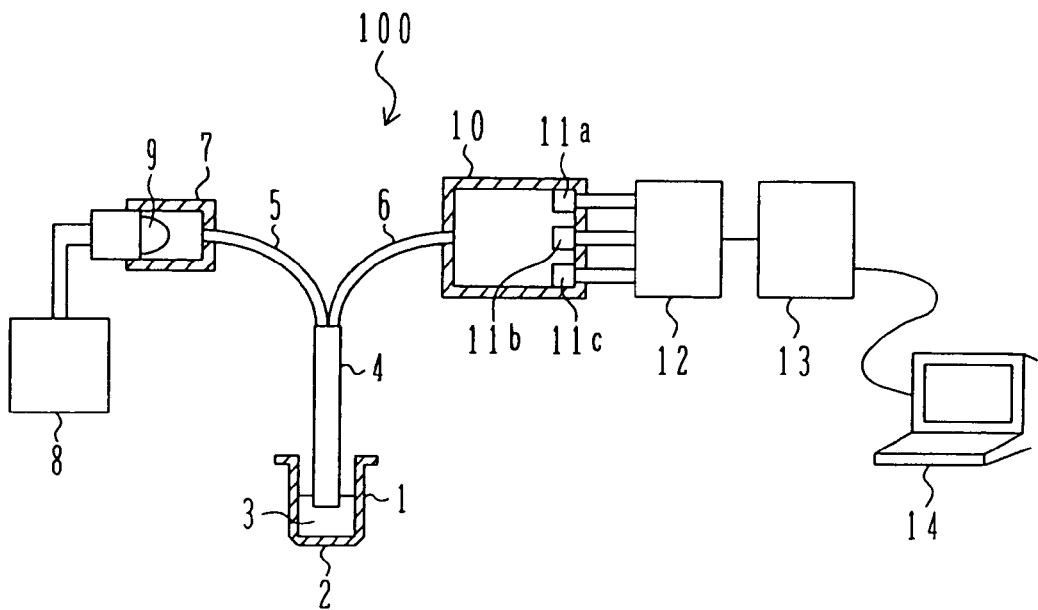
FIG. 1 is a schematic view of a measuring device for biomolecular interaction analysis according to one embodiment of the present invention.

Measuring devices for biomolecular interaction analysis according to several embodiments of the present invention will be described below with reference to the drawings. FIG. 1 is a schematic view of a measuring device for biomolecular interaction analysis, i.e., a device 100 for measuring a biomolecular binding amount, according to one embodiment of the present invention. A sensor well 1 serving as a container for containing an analysis sample 3 to be measured is in the form similar to a sample plate usually used in biochemical analysis. A noble metal nanoparticle sensor 2 similar to that disclosed in the above-cited Patent Document 1 (JP,A 2000-55920) is formed at the bottom of the sensor well 1. The surface of the noble metal nanoparticle sensor 2 is chemically modified or includes an analyte material fixed to it, e.g., an antigen, depending on the analysis purpose. In this embodiment, a running buffer, e.g., a phosphate buffer solution, is used as the analysis sample 3.

A measuring probe 4 is inserted in the sensor well 1, and a tip of the measuring probe 4 is placed in the running buffer 3. An irradiation optical fiber 5 and a measurement optical fiber 6 are held in the measuring probe 4. The irradiation optical fiber 5 and the measurement optical fiber 6 are arranged so as to face the noble metal nanoparticle sensor 2.

One end of the irradiation optical fiber 5 is immersed in the running buffer 3, and the other end of the irradiation optical fiber 5 is extended externally of the measuring probe 4 and connected to an LED holder 7. A white LED 9 driven by a light emitting circuit 8 is mounted in the LED holder 7. White light emitted under operation of the light emitting circuit 8 is irradiated to the surface of the noble metal nanoparticle sensor 2 through the measuring probe 4.

Also, the measurement optical fiber 6 has one end immersed in the running buffer 3 and the other end extended from the measuring probe 4 and connected to a photosensor holder 10. A plurality of photodiodes 11a-11c provided with filters having different passage wavelengths are held inside the photosensor holder 10. The light emitted from the white LED 9 and reflected by the surface of the noble metal nanoparticle sensor 2 is introduced to the photodiodes 11a-11c through the measurement optical fiber 6. The photodiodes 11a-11c receive lights in respective wavelength bands after filtering through the associated filters and generate currents corresponding to the intensities of the received lights. The generated currents are converted to voltages and are amplified by an amplification circuit 12. The amplified voltages are inputted to a data processing unit 14 via an interface circuit 13.

Figure 2:
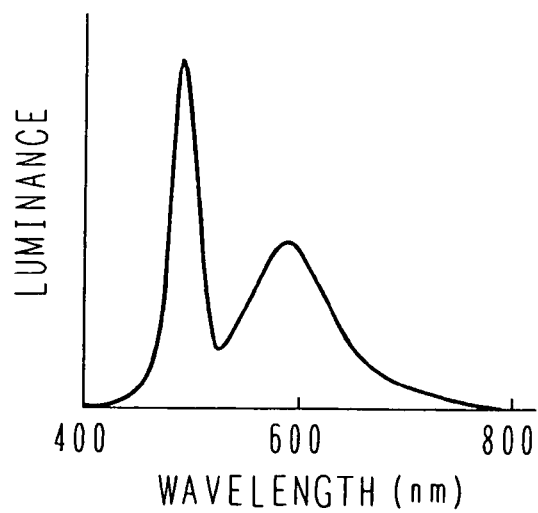
FIG. 2 is a graph for explaining a wavelength characteristic of a white LED used in the measuring device for biomolecular interaction analysis shown in FIG. 1.
Figure 3:
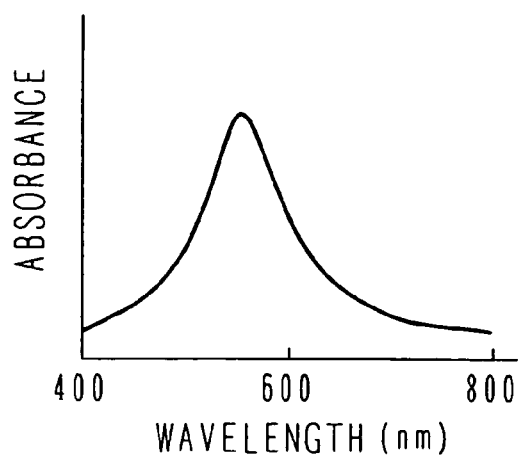
FIG. 3 is a graph for explaining an absorption wavelength characteristic of a noble metal nanoparticle sensor used in the measuring device for biomolecular interaction analysis shown in FIG. 1.

The operation of the measuring device for biomolecular interaction analysis according to this embodiment will be described below. FIG. 2 shows a wavelength characteristic of the white LED 9 held in the LED holder 7, and FIG. 3 shows an absorbance spectrum characteristic of the reflected light from the noble metal nanoparticle sensor 2. The white LED 9 can be constituted by adding a yellow phosphor to the so-called blue LED. The white LED 9 used in this embodiment emits light over a wavelength band of about 400-800 nm. When the emitted light is irradiated to the noble metal nanoparticle sensor 2 with a particle size of about 110 nm, an absorbance spectrum of the reflected light is obtained which has an absorption peak at a wavelength of about 550 nm, as shown in FIG. 3.

In consideration of the above, the wavelength filters applied to the photodiodes 11a-11c contained in the photosensor holder 10 are selected based on the absorbance spectrum shown in FIG. 3. More specifically, three filters are selected with respect to the peak wavelength of the white LED 9 shown in FIG. 2, i.e., a first filter covering a wavelength band longer than the peak wavelength, a second filter covering a wavelength band including the peak wavelength, and a third filter covering a wavelength band shorter than the peak wavelength. In other words, the selected three filters have spectral sensitivity characteristics 401-403 shown in FIG. 4. The first filter is set to have a central wavelength near 620 nm corresponding to the spectral sensitivity characteristic 401, the second filter is set to have a central wavelength near 550 nm corresponding to the spectral sensitivity characteristic 402, and the third filter is set to have a central wavelength near 460 nm corresponding to the spectral sensitivity characteristic 403. Those wavelength bands are almost the same as those of the three primary colors, i.e., red, green and blue. Therefore, an ordinary RGB color filter can be used.

The data processing unit 14 calculates absorbance $A(\lambda)$ in each wavelength band from the intensities of the reflected lights received by the photodiodes 11a-11c based on the following formula (1):

$$A(\lambda) = -\log\left[L(\lambda)/\{R(\lambda) - d(\lambda)\}\right] \quad (1)$$

In the formula (1), $\lambda$ represents the wavelength band and is given as $\lambda 1$, $\lambda 2$ and $\lambda 3$ representing the wavelength bands of the first to third filters, respectively. $R(\lambda)$ represents the intensity of light measured in advance by using a reference reflection plate having the known reflectance, $d(\lambda)$ represents the intensity of light measured in advance without irradiating light, and $L(\lambda)$ represents the intensity of light measured by using the photodiodes 11a-11c.

Figure 5:
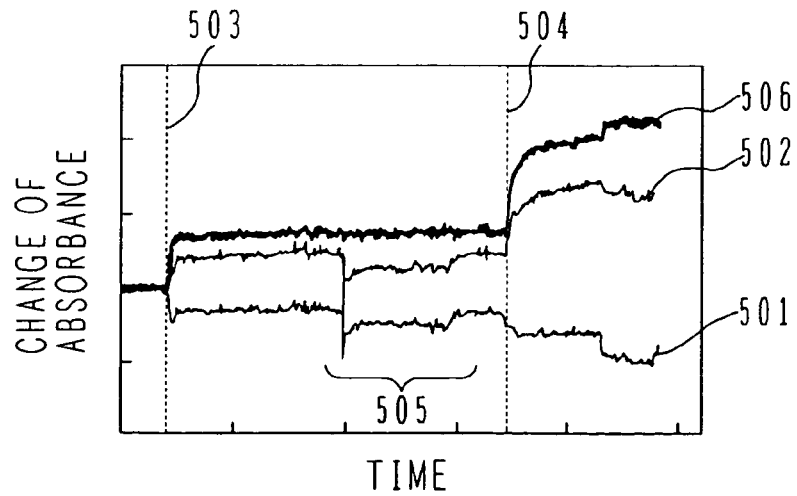
FIG. 5 is a graph showing an example of measurement by the measuring device for biomolecular interaction analysis shown in FIG. 1.

On an assumption that a change of the absorbance $A(\lambda)$ calculated based on the formula (1) is $\Delta A(\lambda)$, a variation of the change $\Delta A(\lambda)$ over time is shown in the graph of FIG. 5. In an initial state, a sufficient amount of the running buffer 3 is held in the sensor well 1. In such an initial state, an absorbance change 501 detected by the photodiode 11c provided with the third filter and an absorbance change 502 detected by the photodiode 11a provided with the first filter are both hardly varied.

At a time 503 after the lapse of a predetermined time, an antigen (not shown) is put in the running buffer 3. The antigen starts to adsorb onto the surface of the noble metal nanoparticle sensor 2. Correspondingly, the absorption peak wavelength of the noble metal nanoparticle sensor 2 is shifted toward the longer wavelength side. At this time, the absorbance change 501 detected by the photodiode 11c covering the shorter wavelength band decreases and the absorbance change 502 detected by the photodiode 11a covering the longer wavelength band increases. An amount of decrease and increase in the absorbance change depends on an amount of the adsorbed antigen.

After replacing a solution containing the antigen with the running buffer 3, an antibody substance capable of binding to the antigen substance is added to the running buffer 3 at a time 504. The added antibody substance is bound to the antigen substance adsorbed on the surface of the noble metal nanoparticle sensor 2. At this time, the absorbance change 501 detected by the photodiode 11c covering the shorter wavelength band decreases and the absorbance change 502 detected by the photodiode 11a covering the longer wavelength band increases depending on a binding amount of the antibody substance to the antigen substance.

During a period 505 in FIG. 5, there occur variations in no relation with the biomolecular binding. Those variations are caused by mixing or replacement of the solution, fluctuations of the light source, and other factors. During the period 505, the absorption peak wavelength is hardly varied. The overall absorbance is varied. Further, the absorbance change 501 detected by the photodiode 11c covering the shorter wavelength band and the absorbance change 502 detected by the photodiode 11a covering the longer wavelength band are both decreased or increased in a similar pattern.

To remove those noise components, the difference between the absorbance change 501 detected by the photodiode 11c covering the shorter wavelength band and the absorbance change 502 detected by the photodiode 11a covering the longer wavelength band is calculated. On that occasion, because the absorbance changes 501, 502 detected by the photodiodes 11c, 11a covering the shorter and longer wavelength bands with respect to the change of the peak wavelength are varied depending on the magnitude of the absorbance at the peak wavelength, the absorbance changes 501, 502 are normalized by using the absorbance detected by the photodiode 11b corresponding to the peak wavelength. As a result, a binding signal U can be calculated, for example, from the following formula (2):

$$U=\Delta A(\lambda 3)/(A(\lambda 2)-A(\lambda 3))-\Delta A(\lambda 1)/(A(\lambda 2)-A(\lambda 1)) \quad (2)$$

The calculated binding signal U is indicated by data 506 in FIG. 5. The noises occurred during the period 505 are cancelled and an improved signal is obtained.

According to this embodiment, since the biomolecular binding amount on the surface of the noble metal nanoparticle sensor 2 is measured by using a plurality of detectors provided with filters having different passage wavelengths, it is possible to eliminate influences of the magnitude of the peak absorbance and fluctuations caused by disturbances. When quality of the noble metal nanoparticle sensor 2 is uniform and the peak absorbance can be held substantially constant, the influence of the magnitude of the peak absorbance is negligible and the binding signal U can be calculated from the following formula (3);

$$U=\Delta A(\lambda 3)-K\Delta A(\lambda 1) \quad (3)$$

where K is a constant for normalizing a change $\Delta A(\lambda i)$ of the peak absorbance.

With the peak absorbance being substantially constant, the photodiode 11b is not required. Therefore, the measuring device for biomolecular interaction analysis can be further simplified and reduced in size. Also, noises other than the binding signal can be suppressed by properly selecting a solution pouring method. In this case, because of no need of calculating the difference in absorbance between two wavelength bands, the binding signal U can be obtained by using either one of the photodiodes 11c, 11a covering the shorter and longer wavelength bands.

While, in this embodiment, the sensor fabricated according to the method disclosed in Patent Document 1 is used to analyze biomolecular interactions with the aid of noble metal nanoparticles, the present invention is not limited to that type of sensor. For example, a biosensor fabricated by using gold colloid or by forming a metal film having patterned small slits employs a metal material having rugged shapes smaller than the wavelength of visible light and exhibits optical properties similar to those of noble metal nanoparticles. Accordingly, such a biosensor is also usable as the optical biosensor in the measuring device for biomolecular interaction analysis.

Figure 6:
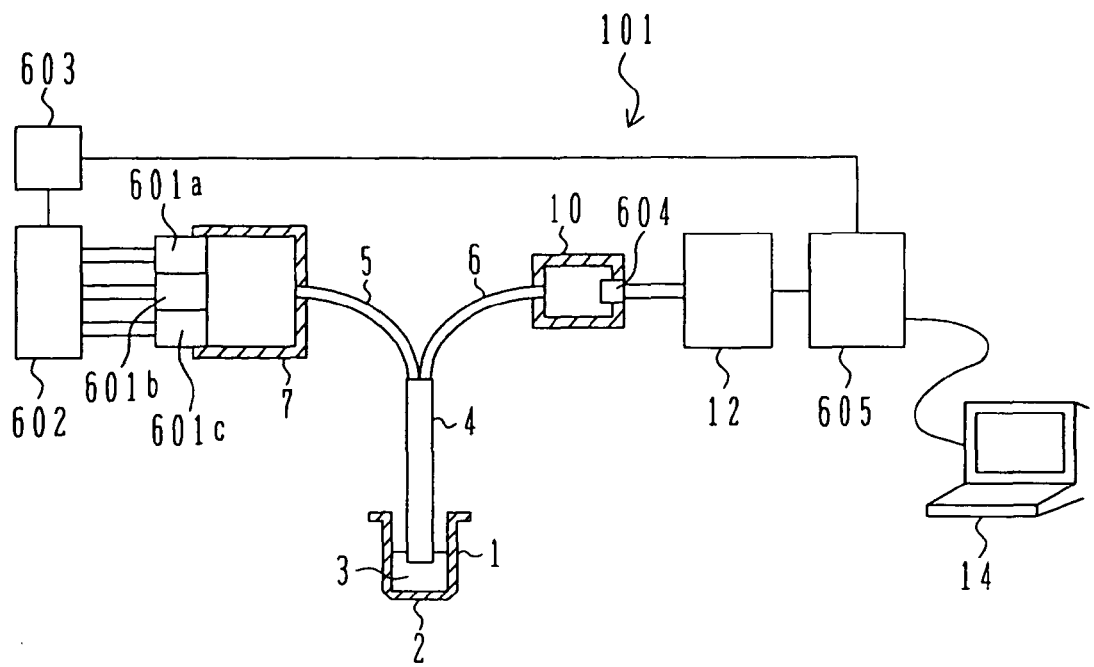
FIG. 6 is a schematic view of a measuring device for biomolecular interaction analysis according to another embodiment of the present invention.

FIG. 6 is a schematic view of a measuring device for biomolecular interaction analysis according to another embodiment of the present invention. The optical biosensor 101 for biomolecular interaction analysis according to this embodiment differs from that according to the above-described embodiment in the following point. An LED holder 7 contains three LED's for emitting lights with different wavelength characteristics. More specifically, a blue LED 601a having a light emission wavelength characteristic 701 shown in FIG. 7, a green LED 601b having a light emission wavelength characteristic 702, and a red LED 601c having a light emission wavelength characteristic 703 are held in the LED holder 7.

Those wavelength characteristics of the LED's 601a-601c are substantially matched with the characteristics of the wavelength filters for the photodiodes 11a-11c used in the above-described embodiment. The blue LED 601a, the green LED 601b, and the red LED 601c are individually controlled by a light emission circuit 602 and a synchronization circuit 603. Those three LED's 601a-601c are sequentially energized to emit lights at constant intervals.

In a photosensor holder 10, a wide-band photodiode 604 is mounted which covers all of light emission wavelength bands of the blue LED 601a, the green LED 601b, and the red LED 601c. A light reception signal from the photodiode 604 is amplified by an amplification circuit 12 and is inputted to a synchronous interface circuit 605. In the synchronous interface circuit 605, measurement data detected by the photodiode 604 is allocated to the three wavelength bands in accordance with a synchronizing signal transmitted from the synchronization circuit 603 and then sent to a data processing unit 14. By setting the interval between the light emissions from the three LED's 601a-601c to be sufficiently short, data representing the intensities of the receives lights in the three wavelength bands are obtained which are substantially the same as those obtained in the embodiment shown in FIG. 1.

The sensitivity of the photodiode 604 depends on its light receiving area. According to this embodiment, the light receiving area of the photodiode 604 can be fully utilized for the measurement in each of the three wavelength bands, and therefore the sensitively can be increased. While a data processing manner executed by the data processing unit 14 in this embodiment is the same as that in the above-described embodiment, the number of LED's can be reduced or increased, as required, depending on the kind of target and particulars of the measurement. When the number of LED's is reduced, the sensor construction can be simplified correspondingly.

Figure 8:
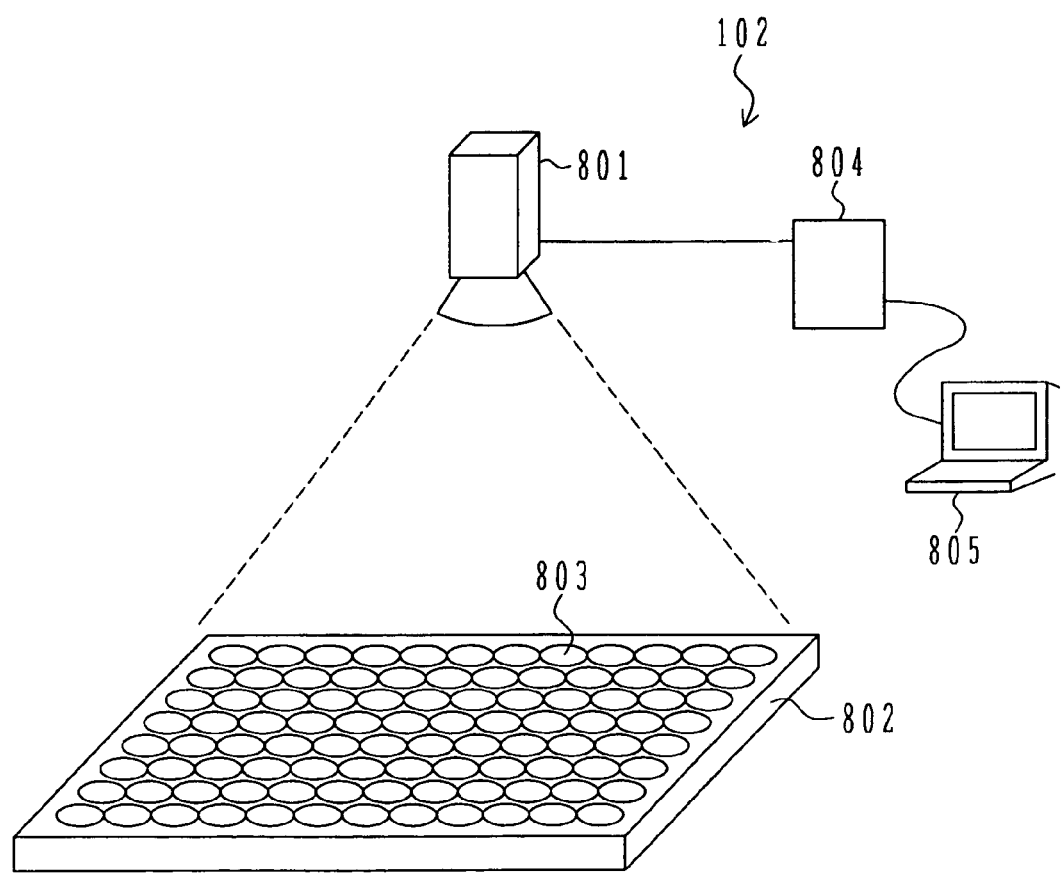
FIG. 8 is a schematic view of a measuring device for biomolecular interaction analysis according to still another embodiment of the present invention.

FIG. 8 is a schematic view of a measuring device for biomolecular interaction analysis according to still another embodiment of the present invention. The measuring device 102 for biomolecular interaction analysis according to this embodiment differs from the measuring devices according to the above-described embodiments in means for measuring the reflected light from the noble metal nanoparticles. While the above-described embodiments use the photodiode(s) to detect the intensity of the reflected light from the noble metal nanoparticles, a color CCD camera 801 is used as detecting means in this embodiment. In the color CCD camera 801, CCD elements for measuring the intensities of respective wavelengths of the three primary colors (RGB) are arranged in a two-dimensional array. Because the individual CCD elements are able to measure the reflected light from the noble metal nanoparticles, a sensor array plate 802 is used instead of the sensor well.

On the sensor array plate 802, noble-metal-nanoparticle sensor spots 803 are two-dimensionally arranged in a plane.

More specifically, a large number of noble-metal-nanoparticle sensor spots 803 are formed on the sensor array plate 802. Each of the sensor spots 803 serves as the sensor well. In a preparation step for the measurement, different kinds of chemical substances or high biomolecules employed for analysis of binding are fixed to the noble-metal-nanoparticle sensor spots 803 by using a pipette or a spotting machine. Thereafter, a biomolecular sample for which binding to the fixed chemical substances or high biomolecules is to be analyzed is coated on an upper surface of the sensor array plate 802. As an alternative, the sensor array plate 802 may be immersed in a sample solution (not shown).

Figure 4:
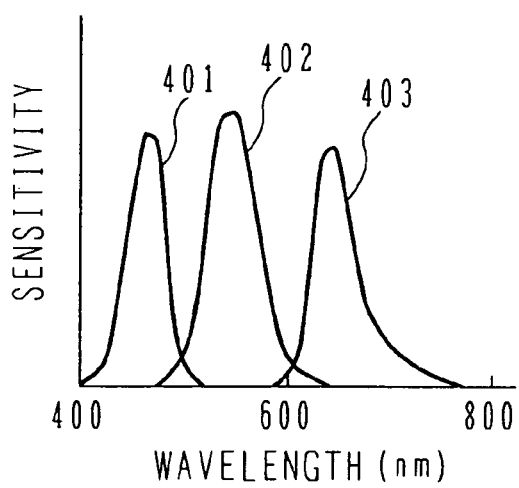
FIG. 4 is a graph for explaining a sensitivity characteristic of a photosensor used in the measuring device for biomolecular interaction analysis shown in FIG. 1.
Figure 7:
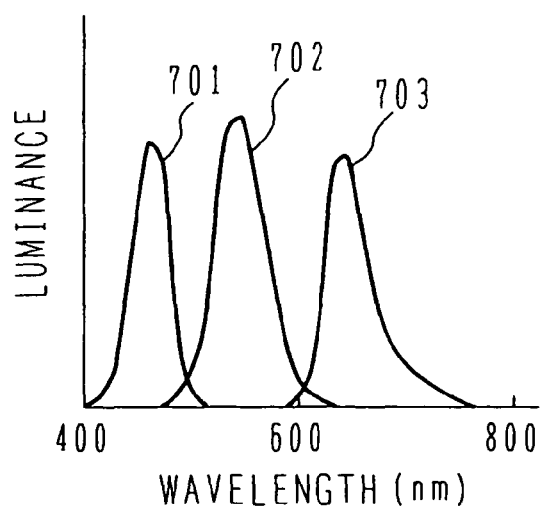
FIG. 7 is a graph for explaining wavelength characteristics of LED's in respective colors used in the measuring device for biomolecular interaction analysis shown in FIG. 6.

The state of the sensor array plate 802 is measured by the color CCD camera 801. Images of the noble-metal-nanoparticle sensor spots 803 on the sensor array plate 802 are picked up and transmitted to a data processing unit 805 via an interface board 804. The data processing unit 805 executes image processing for RGB values obtained from the noble-metal-nanoparticle sensor spots 803. As a result, similar signals to those representing the intensities of the received lights in the respective wavelength bands, shown in FIGS. 4 and 7, are obtained for all of the noble-metal-nanoparticle sensor spots 803 on the sensor array plate 802.

According to this embodiment, because of using the noble metal nanoparticle sensor formed on an array plate or in a micro-channel in a matrix pattern, simultaneous multipoint measurement can be performed with high efficiency. While, in this embodiment, the color CCD camera measures all of the noble-metal-nanoparticle sensor spots on the sensor array plate, it is also of course possible to increase the number of times of measurements and to perform the processing in a split manner.

What is claimed is:

1. A measuring device for biomolecular interaction analysis, said device comprising:
   an optical biosensor having a surface of which optical characteristics are changed with adsorption of a substance onto the surface; and
   an optical measuring device for measuring the optical characteristics of the surface of said optical biosensor, said optical measuring device being arranged to receive light of multiple wavelengths from the surface of said optical biosensor, determine absorbance changes at the multiple wavelengths, and remove noise from the optical characteristic measurement,
   wherein said optical measuring device is arranged to measure the intensity of light outputted from said optical biosensor in a second band including a maximum absorption wavelength, a first band covering a longer wavelength range than the maximum absorption wavelength, and a third band covering a shorter wavelength range than the maximum absorption wavelength,
   and wherein said measuring device further comprises:
   a first optical sensor element for measuring an intensity of light in said first band;
   a second optical sensor element for measuring an intensity of light in said second band;
   a third optical sensor element for measuring an intensity of light in said third band; and
   a data processing unit for calculating absorbance $A(\lambda 1)$, $A(\lambda 2)$, and $A(\lambda 3)$ in said first band, said second band, and said third band, respectively, from intensity lights measured by said first optical sensor element, said second optical sensor element, and said third optical sensor element on the basis of the following formula (1), $$A(\lambda) = -\log[L(\lambda)/\{R(\lambda)-d(\lambda)\}] \quad (1),$$

$\lambda$ representing wavelength bands of said first wavelength band $\lambda 1$, said second wavelength band $\lambda 2$ and said third wavelength band $\lambda 3$, $R(\lambda)$ representing an intensity of light measured by using a reference reflection plate having a known reflection, $d(\lambda)$ representing and intensity of light measured without irradiating light, $L(\lambda)$ representing an intensity of light measured by using said first optical sensor element, said second optical sensor element, and said third optical sensor element, said data processing, unit calculating changes of absorbance $A(\lambda 1)$ and $A(\lambda 3)$, calculating a binding signal U on the basis of following formula (2), $$U = \Delta A(\lambda 3)/(A(\lambda 2)-A(\lambda 3)) - \Delta A(\lambda 1)/(A(\lambda 2)-A(\lambda 1)) \quad (2)$$

$\Delta A(\lambda 1)$ and $\Delta A(\lambda 3)$ representing changes of absorbance $A(\lambda 1)$ and $A(\lambda 3)$.

2. The measuring device for biomolecular interaction analysis according to claim 1, further comprising a light source for irradiating light to said optical biosensor, and a filter allowing passage of light only in a particular wavelength band and disposed in said optical measuring device.

3. The measuring device for biomolecular interaction analysis according to claim 2, wherein said light source has a light emission characteristic in a particular wavelength band.

4. The measuring device for biomolecular interaction analysis according to claim 2, wherein said measuring device includes a plurality of light sources having characteristics to emit lights in respective different wavelength bands, and a controller for synchronizing a light emission time of each of said plurality of light sources with a measurement time of said optical measuring device.

5. A measuring device for biomolecular interaction analysis, said device comprising:
   an optical biosensor having a surface of which optical characteristics are changed with adsorption of a substance onto the surface; and
   an optical measuring device for measuring the optical characteristics of the surface of said optical biosensor, said optical measuring device being arranged to receive light of multiple wavelengths from the surface of said optical biosensor, determine absorbance changes at the multiple wavelengths, and remove noise from the optical characteristic measurement,
   wherein said optical measuring device is arranged to measure the intensity of light outputted from said optical biosensor in a second band including a maximum absorption wavelength, a first band covering a longer wavelength range than the maximum absorption wavelength, and a third band covering a shorter wavelength range than the maximum absorption wavelength,
   and wherein the measuring device further comprises:
   a first optical sensor element for measuring an intensity of light in said first band;
   a second optical sensor element for measuring an intensity of light in said second band;
   a third optical sensor element for measuring an intensity of light in said third band; and
   a data processing unit for calculating absorbance $A(\lambda 1)$, $A(\lambda 2)$, and $A(\lambda 3)$ in said first band, said second band, and said third band, respectively, from intensity of lights measured by said first optical sensor element, said second optical sensor element, and said third optical sensor element on the basis of the following formula (1), $$A(\lambda) = -\log[L(\lambda)/\{R(\lambda)-d(\lambda)\}] \tag{1}$$

$\lambda$ representing wavelength bands of said first wavelength band $\lambda 1$, said second wavelength band $\lambda 2$, and said third wavelength $\lambda 3$, $R(\lambda)$ representing an intensity of light measured by using a reference reflection plate having a known reflection, $d(\lambda)$ representing an intensity of light measured without irradiating light, $L(\lambda)$ representing an intensity of light measured by using said first optical sensor element, said second optical sensor element, and third optical sensor element, said data processing unit calculating changes of absorbance $A(\lambda 1)$ and $A(\lambda 3)$, calculating a binding signal U on the basis of following formula (3), $$U = \Delta A(\lambda 3) - K \Delta A(\lambda 1) \tag{3}$$

$\Delta A(\lambda 1)$ and $\Delta A(\lambda 3)$ representing changes of absorbance $A(\lambda 1)$ and $A(\lambda 3)$, K representing changes of a constant for normalizing a change $\Delta A(\lambda)$ of peak absorbance.

* * * * *